June 7, 1955 H. R. SCHENKEL Plant Pat. 1,398
ROSE PLANT
Filed Oct. 21, 1954
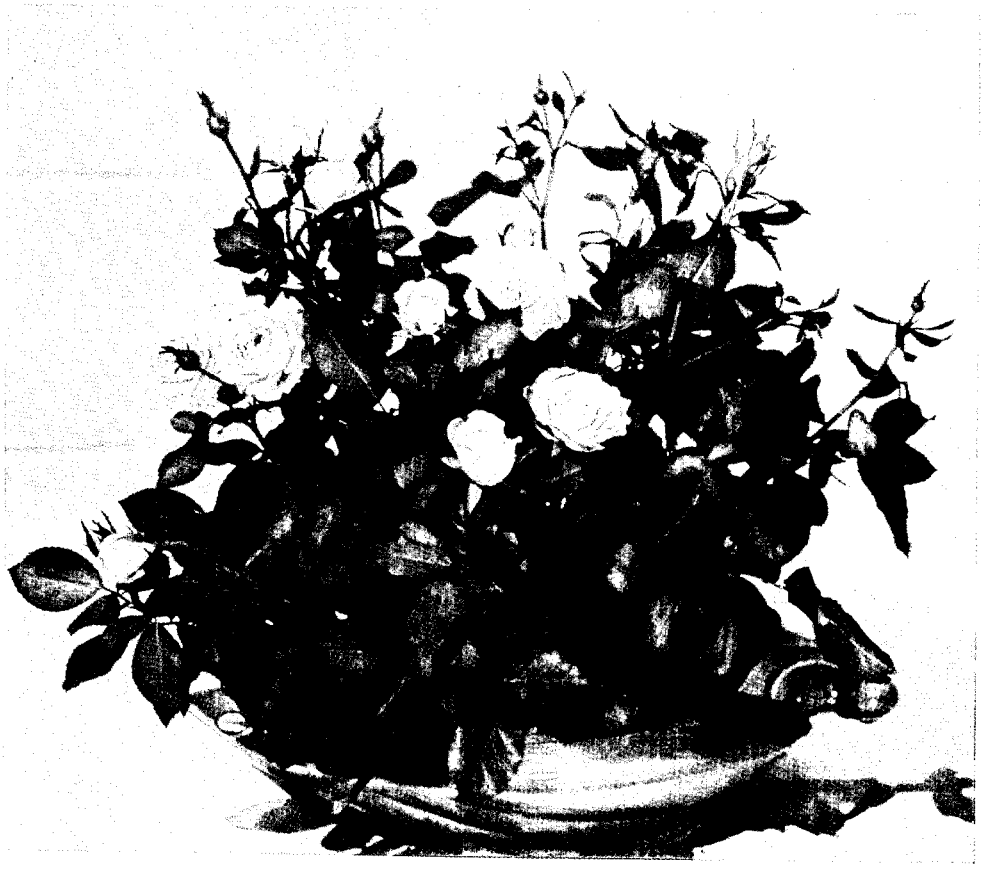
Inventor.
H. R. Schenkel
By: Robb & Robb
Attorneys.

United States Patent Office

Plant Pat. 1,398
Patented June 7, 1955

1,398

ROSE PLANT

Herman R. Schenkel, Lynchburg, Va.

Application October 21, 1954, Serial No. 463,841

1 Claim. (Cl. 47—61)

The present invention relates to a new and distinct variety of rose plant of the large-flowered polyantha class, which was originally discovered by me amongst my regular greenhouse plantings of the variety "Garnette" (unpatented), at Lynchburg, Virginia.

My attention was initially directed to the new variety by the fact that one of the greenhouse plants of "Garnette" produced a stem which bore foliage distinctly different in color in the young stage, as compared with the normal color of the variety "Garnette," the color of said young foliage being brownish instead of the characteristic Red color of "Garnette." Upon observing this difference, I marked the plant and the particular stem as a precaution against inadvertent cutting thereof, and continued to closely observe the same until the stem came into flower, at which time, I found that the stem bore distinctive Pink flowers quite different from the characteristic color of the flowers of the parent variety "Garnette." Thereupon, I carefully nurtured and propagated the sport by budding, at Lynchburg, Virginia, and ultimately established to my complete satisfaction that the novel features and distinctions of the sport, as aforementioned, came true to form and were established and transmissible by asexual reproduction. Continued propagation has further established that the new variety is an even better producer of flowers of long-lasting quality, without fading of the flower color, than its parent variety "Garnette" which is so well-known for its free flower production and the lasting qualities of its flowers.

All of the foregoing characteristics and distinctions of my new variety, when taken together, definitely establish that my new variety is distinctly different from its parent, as well as from all other varieties of its class of which I am aware.

The accompanying drawing shows typical specimens of the flowers and foliage of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Sport of "Garnette."
Classification:
*Botanic.*—Large-flowered polyantha.
*Commercial.*—Floribunda.

FLOWER (Observations made in a greenhouse at Newark, New York, in the early morning, during the early part of the month of July.)

Blooming habit: Recurrent—continuous; very free in greenhouse; flowers appear on all new shoots.
Bud:
*Size.*—Medium.
*Form.*—Ovoid; is not affected by wet or hot weather.
*Color.*—When sepals first divide—Rose Pink, Plate 12. When petals begin to unfurl—Thulite Pink, Plate 26. When half bloom: Inside of petals—Thulite Pink, Plate 26, lightly overcast with Cameo Pink, Plate 26; reverse of petals—Thulite Pink, Plate 26.
*Sepals.*—Branched; curl back when petals begin to unfurl. Color: Inside—Light Cress Green, Plate 31; outside—Kildare Green, Plate 31.
*Calyx.*—Color—Glass Green, Plate 31. Shape—funnel. Size—small. Aspect—smooth. Odor when rubbed—none.
*Peduncle.* — Length — short. Aspect — rough. Strength—bending; slender. Color—Absinthe Green, Plate 31.
*Opening.*—Opens up well; is not affected by adverse weather conditions.

Bloom:
*Size.—Medium.* Average size when fully expanded—2½ inches.
*Borne.*—Several together and in irregular clusters.
*Stems.*—Medium length; medium strength.
*Form (when first open).*—Flat. Permanence—flattens, with outer petals curling back.
*Petalage.*—Double (full but open center). Number of petals under normal conditions—from 55 to 60.
*Color.*—Center of flower—Thulite Pink, Plate 26. Outer petals—Cameo Pink, Plate 26. Base of petals (aiglet)—Light Yellow Green, Plate 6. Inside of petals—Rose Pink, Plate 12. Reverse of petals—Cameo Pink, Plate 26. General tonality from a distance—Rose Pink, Plate 12.
*Discoloration.*—General tonality at end of first day—Thulite Pink, Plate 26. Second day—Rose Pink, Plate 12. Third day—Rose Pink, Plate 12, lightly overcast with Cameo Pink, Plate 26.

Petals:
*Texture.*—Leathery; is not affected by wet or hot weather.
*Appearance.*—Inside satiny and outside satiny.
*Form.*—Oval.
*Arrangement.*—Irregular.
*Petaloids in center.*—Few; small.
*Persistence.*—Drop off cleanly.
*Fragrance.*—Moderate. Nature—tea (average hybrid tea scent).
*Lasting quality.*—On the plant—very long; as cut flower—very long.

GENITAL ORGANS

Stamens, anthers: Medium size; few; regular around styles. Color—Ochraceous—Orange, Plate 15.
Stamens, filaments (threads): Medium length. Color—Veronese Green, Plate 18.
Pollen: Color—Pale Ochraceous Salmon, Plate 15.
Styles: Bunched; uneven length; medium length; thin.
Stigmas: Color—Naples Yellow, Plate 16.
Ovaries: All enclosed in calyx.
Hips: None.
Seeds: None.

PLANT

Form: Bush.
Growth: Vigorous; branching; very free-branching in greenhouse.
Foliage: 5 to 7 leaflets.
*Size.*—Medium.
*Quantity.*—Normal.
*Color.*—New foliage: Upper side—Hay's Maroon, Plate 13; under side—Yellowish Oil Green, Plate 5, overcast with Cameo Brown, Plate 28. Old foliage: Upper side—Varley's Green, Plate 18; under side—Chromium Green, Plate 32.

*Shape.*—Oval.

*Texture.* — Upper side — leathery; under side — smooth.

*Ribs and veins.*—Ordinary.

*Edge.*—Serrated (saw-toothed).

*Serration.*—Both double and single; small.

*Leaf stem.*—Color—Kildare Green, Plate 31. Under side—Prickles.

*Stipules.*—Medium length; serrated.

Wood:

*New wood.*—Color—Mignonette Green, Plate 31. Bark—smooth.

*Old wood.*—Color—Cress Green, Plate 31. Bark—smooth.

Thorns:

*Thorns.*—Quantity: On main stalks from base—ordinary; on laterals from statk — ordinary. Form—flat base; medium length; some hooked downward and some hooked upward. Color (when young)—Kildare Green, Plate 31, with base of Dark Vinaceous, Plate 27. Position—irregular.

*Prickles.*—Quantity: On main stalks—none; on laterals—none.

*Short needles.*—Quantity: On main stalks—none; on laterals—none.

I claim:

A new and distinct variety of rose plant of the large-flowered polyantha class, substantially as herein shown and described, characterized particularly as to novelty by the distinctive color of its foliage and flowers, and by its free production of flowers of long-lasting quality and the absence of fading of the flower color as the flowers age.

No references cited.